(12) United States Patent
Mistretta et al.

(10) Patent No.: US 7,647,088 B2
(45) Date of Patent: Jan. 12, 2010

(54) RECONSTRUCTION METHOD FOR IMAGES OF THE BEATING HEART

(75) Inventors: Charles A. Mistretta, Madison, WI (US); Julia Velikina, Madison, WI (US); Oliver Wieben, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 265 days.

(21) Appl. No.: 11/516,957

(22) Filed: Sep. 7, 2006

(65) Prior Publication Data
US 2007/0167707 A1 Jul. 19, 2007

Related U.S. Application Data

(60) Provisional application No. 60/719,445, filed on Sep. 22, 2005, provisional application No. 60/738,444, filed on Nov. 21, 2005.

(51) Int. Cl.
*A61B 5/055* (2006.01)
(52) U.S. Cl. .................................. 600/428; 600/407
(58) Field of Classification Search ................ 600/428; 382/128
See application file for complete search history.

(56) References Cited

U.S. PATENT DOCUMENTS

| | | | |
|---|---|---|---|
| 4,680,709 A * | 7/1987 | Srinivasan et al. | ............ 378/14 |
| 5,502,385 A | 3/1996 | Kuhn et al. | |
| 5,603,322 A | 2/1997 | Jesmanowicz et al. | |
| 5,604,778 A | 2/1997 | Polacin et al. | |
| 5,933,006 A | 8/1999 | Rasche et al. | |
| 6,490,472 B1 | 12/2002 | Li et al. | |
| 6,807,248 B2 | 10/2004 | Mihara et al. | |
| 6,954,067 B2 | 10/2005 | Mistretta | |
| 7,358,730 B2 * | 4/2008 | Mistretta et al. | ............ 324/307 |
| 2001/0027262 A1 | 10/2001 | Mistretta et al. | |
| 2005/0054916 A1 * | 3/2005 | Mostafavi | .................. 600/427 |
| 2006/0133564 A1 * | 6/2006 | Langan et al. | .................. 378/8 |
| 2006/0274031 A1 * | 12/2006 | Yuen et al. | .................. 345/156 |
| 2007/0010731 A1 * | 1/2007 | Mistretta | .................... 600/407 |

(Continued)

FOREIGN PATENT DOCUMENTS

EP   0 627 633 A1   7/1994

(Continued)

OTHER PUBLICATIONS

Wieslaw L. Nowinski, The Iterated Normalized Backprojection Method of Image Reconstruction, Institute of Computer Science, Polish Academy of Sciences Ordona 21, 01-237 Warsaw, Poland.

(Continued)

*Primary Examiner*—Long V Le
*Assistant Examiner*—Hien Nguyen
(74) *Attorney, Agent, or Firm*—Quarles & Brady LLP

(57) ABSTRACT

Projection views of the moving heart and stationary background tissues are acquired and processed to provide corresponding moving tissue projection views. An average image is reconstructed in a conventional manner and a moving tissue image is reconstructed using a highly constrained backprojection method and a composite image formed from selected moving tissue projection views. The average image is then combined with the moving tissue image. The method is disclosed in a cardiac gated MRI scan.

19 Claims, 11 Drawing Sheets

U.S. PATENT DOCUMENTS

| | | | |
|---|---|---|---|
| 2007/0038373 A1* | 2/2007 | Chen | 701/213 |
| 2007/0156044 A1* | 7/2007 | Mistretta et al. | 600/410 |
| 2007/0167728 A1* | 7/2007 | Mistretta et al. | 600/410 |

FOREIGN PATENT DOCUMENTS

| | | |
|---|---|---|
| WO | WO 2005/026765 | 3/2005 |
| WO | WO 2005/069031 | 7/2005 |

OTHER PUBLICATIONS

Y. Huang et al, Time-Resolved 3D MR Angiography by Interleaved Biplane Projection, Proc. Intl. Soc. Mag. Reson. Med. 13 (2005).

T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

Graeme C. McKinnon et al, Towards Imaging the Beating Heart Usefully with a Conventional CT Scanner, Trans. on Biomedical Eng., vol. BME-28, No. 2, p. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, p. 233-234, Dec. 1986.

A.L. Wentland et al, Technique for Acquiring MR Images of CSF Flow During a Valsalva Maneuver, Med. Phys. Univ. of WI, Madison WI.

K.M. Johnson et al, Average and Time-Resolved Dual Velocity Encoded Phase Contrast Vastly Undersampled Isotropic Projection Imaging, Med. Phys. Univ. of WI, Madison WI.

K.M. Johnson et al, Transtenotic Pressure Gradient Measurements Using Phase Contrast Vastly Undersampled Isotropic Projection Imaging (PC-VIPR) in a Canin Model, Med. Phys. Univ. of WI, Madison WI.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J. Tsao et al, k-t BLAST and k-t SENSE: Dynamic MRI With High Frame Rate Exploiting Spatiotemporal Correlations, Mag. Reson. Med. 50:1031-1042 (2003).

Zhi-Pei Liang et al, Constrained Imaging-Overcoming the Limitations of the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514,Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Ashwani Aggarwal et al, Imaging In Turbid Media by Modified Filtered Back Projection Method Using Data From Monte Carlo Simulation, Proc. of SPIE vol. 5047, pp. 314-324.

Xavier Golay, et al, Presto-Sense: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application To Dynamic Radial Imaging, Proc. Intl. Soc. Mag. Reson. Med. 13 p. 684 (2005).

* cited by examiner

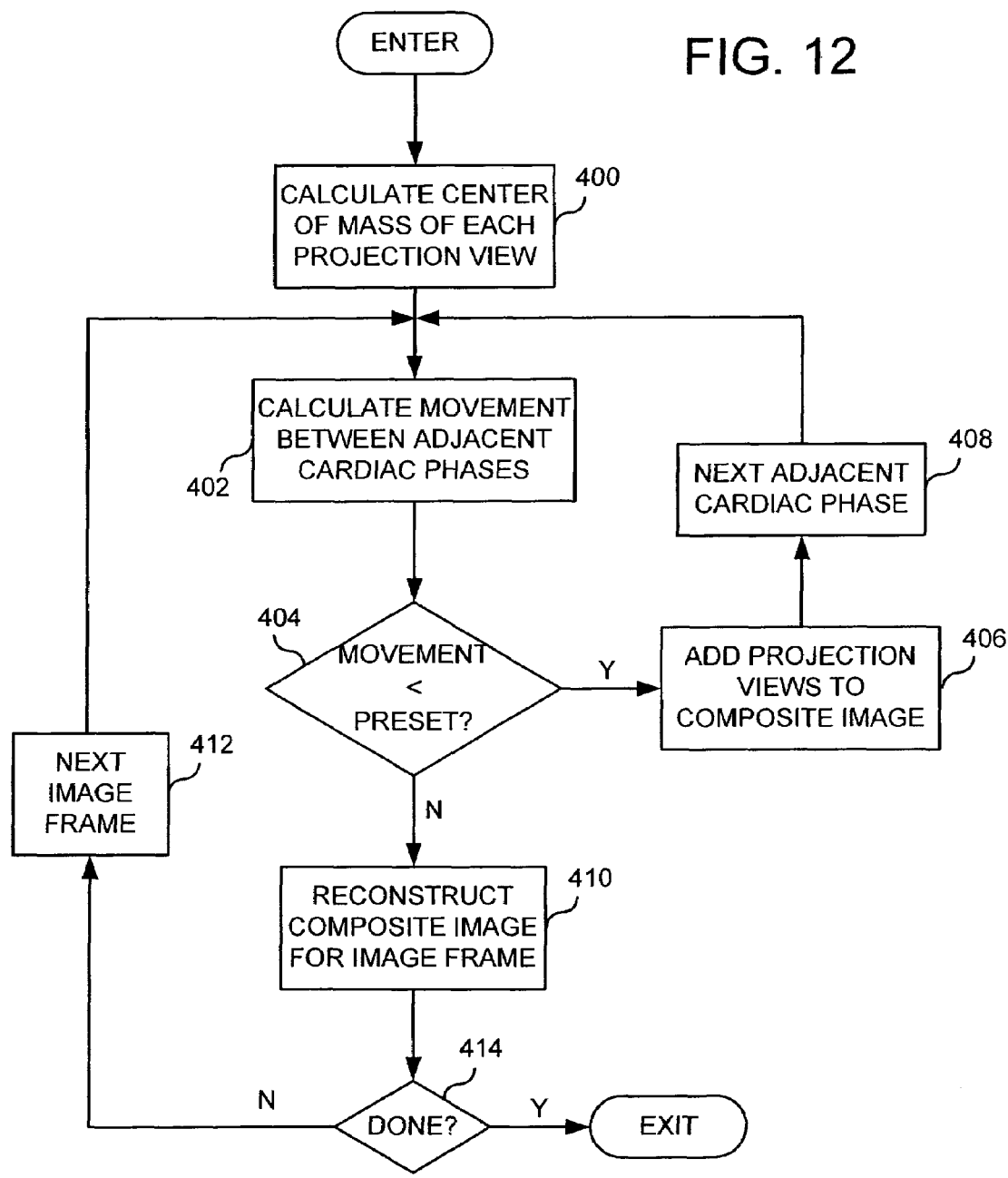

RECONSTRUCTION METHOD FOR IMAGES OF THE BEATING HEART

CROSS-REFERENCE TO RELATED APPLICATIONS

This application is based on U.S. Provisional Patent Application Ser. Nos. 60/719,445 filed on Sep. 22, 2005 and entitled "HIGHLY CONSTRAINED IMAGE RECONSTRUCTION METHOD" and 60/738,444 filed on Nov. 21, 2005 and entitled "IMAGE RECONSTRUCTION METHOD FOR CARDIAC GATED MAGNETIC RESONANCE IMAGING."

STATEMENT REGARDING FEDERALLY SPONSORED RESEARCH

This invention was made with government support under Grant No. NIH HL072260. The U.S. Government has certain rights in this invention.

BACKGROUND OF THE INVENTION

The field of the invention is medical imaging methods and systems. More particularly, the invention relates to the imaging of a moving subject such as the beating heart.

When imaging a moving subject such as the beating heart, higher quality images can be obtained if the data is acquired very rapidly by the medical imaging system. With an x-ray CT system, for example, the x-ray source and detector are rotated around the subject to acquire a sufficient number of projection views from which a tomographic image can be reconstructed. This requires time and a trade-off is usually made between shortening the scan time by acquiring fewer projection views and image quality that improves with more projection views.

While this problem exists for x-ray CT, it is a much more significant problem in magnetic resonance imaging (MRI). When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "stipped", into the x-y plane to produce a net transverse magnetic moment Mt. A signal is emitted by the excited spins after the excitation signal $B_1$ is terminated, this signal may be received and processed to form an image. When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The prevailing methods used to acquire NMR signals and reconstruct images use a variant of the well known Fourier transform (FT) imaging technique, which is frequently referred to as "spin-warp". The spin-warp technique is discussed in an article entitled "Spin-Warp NMR Imaging and Applications To Human Whole-body Imaging" by W. A. Edelstein et al., *Physics in Medicine and Biology*, Vol. 25, pp. 751-756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one Cartesian coordinate system direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of "views" that are acquired during the scan to produce a set of NMR data from which an entire image can be reconstructed.

To increase the rate at which image frames are acquired, image quality may be sacrificed by acquiring fewer phase encoding views, or by using faster pulse sequences that inherently result in lower quality images. With the spin-warp methods, therefore, there is a trade-off between the number of views that are acquired to achieve the desired image resolution and quality, and the rate at which NMR data for a complete image may be acquired.

More recently, an alternative method of acquiring NMR image data has been used in which no phase encoding gradients are employed. Instead, only a readout gradient is applied during the acquisition of each NMR signal (i.e., "view") and a series of different views are acquired by rotating the angle of the readout gradient. Rather than sampling k-space in a rectilinear scan pattern as is done in Fourier imaging, this "projection reconstruction" method samples k-space with a series of views that sample radial lines extending outward from the center of k-space. The number of views needed to sample k-space determines the length of the scan and if an insufficient number of views are acquired, streak artifacts are produced in the reconstructed image.

Because the beating heart is constantly moving, the many different views needed to reconstruct an artifact-free image are acquired over a series of heart beats at approximately the same point, or "sphase", in the cardiac cycle. Image acquisition is gated using an ECG trigger signal, and typically four to eight views (referred to as a "segment") are acquired at a selected time interval after the cardiac trigger signal. The reconstructed image depicts the heart at a particular cardiac phase as determined by the selected delay time.

The standard backprojection method used in both MRI and x-ray CT is illustrated in FIG. 2. Each acquired signal projection profile 10 is backprojected onto the field of view 12 by projecting each signal sample 14 in the profile 10 through the FOV 12 along the projection path as indicted by arrows 16. In projecting each signal sample 14 in the FOV 12 we have no a priori knowledge of the subject and the assumption is made that the signals in the FOV 12 are homogeneous and that the signal sample 14 should be distributed equally in each pixel through which the projection path passes. For example, a projection path 18 is illustrated in FIG. 2 for a single signal sample 14 in one signal projection profile 10 as it passes through N pixels in the FOV 12. The signal value (P) of this signal sample 14 is divided up equally between these N pixels:

$$S_n = (P \times 1)/N \tag{1}$$

where: $S_n$ is the NMR signal value distributed to the $n^{th}$ pixel in a projection path having N pixels.

Clearly, the assumption that the signal in the FOV 12 is homogeneous is not correct. However, as is well known in the art, if certain filtering corrections are made to each signal profile 10 and a sufficient number of filtered profiles are acquired at a corresponding number of projection angles, the errors caused by this faulty assumption are minimized and image artifacts are suppressed. In a typical, filtered backprojection method of image reconstruction, 400 projections are required for a 256×256 pixel 2D image and 203,000 projections are required for a 256×256×256 voxel 3D image. If the method described in the above-cited U.S. Pat. No. 6,487,435 is employed, the number of projection views needed for these same images can be reduced to 100 (2D) and 2000 (3D).

More than 20 years ago a method was proposed for reducing the number of projection views needed to produce adequate images of the beating heart, McKinnon and Bates "Towards Imaging The Beating Heart Usefully With A Conventional CT Scanner", IEEE Transactions on Biomedical Engineering, Vol. BME-28, No. 2, Feb. 1981. The authors recognized that when acquiring views at different cardiac phases the stationary tissues surrounding the heart remained constant throughout and all the acquired views could be used to reconstruct a very high quality image of the stationary tissues. By combining the higher quality stationary tissue image data with the acquired moving tissue data an image could be reconstructed in which streak artifacts caused by stationary tissues could be removed. This method has not found significant clinical use, however, because the multisource CT scanner for which the method was designed was not commercialized.

While a decent single-slice, 2D image may be acquired at one or more cardiac phases during a single breath-hold using known methods, prior methods are not fast enough to acquire a 3D image or multiple 2D slices at each cardiac phase during a single breath hold. Such images are necessary when the subject of the examination (such as coronary arteries) does not lie in a single 2D plane and either a multi-slice or 3D image acquisition is needed to make a diagnoses.

SUMMARY OF THE INVENTION

The present invention is a new method for producing images of the heart and other moving tissues, and particularly a method for improving the quality of highly undersampled images acquired at specific cardiac phases. A series of undersampled image frames are acquired at a selected cardiac phase during successive heart beats. The views acquired during successive heart beats sample interleaved trajectories in k-space and these are combined and used to reconstruct a composite image that depicts the subject. This composite image is used to reconstruct an image frame from the acquired image frame views by using a highly constrained backprojection method in combination with the McKinnon and Bates method.

A discovery of the present invention is that good quality frame images can be produced with far fewer acquired views if a priori knowledge of the signal contour in the FOV 12 is used in the backprojection image reconstruction process instead of the assumed homogeneous signal contour. Referring to FIG. 3, for example, the signal contour in the FOV 12 may be known to include structures such as blood vessels 18 and 20. That being the case, when the backprojection path 8 passes through these structures a more accurate distribution of the signal sample 14 in each pixel is achieved by weighting the distribution as a function of the known NMR signal contour at that pixel location. As a result, a majority of the signal sample 14 will be distributed at the pixels that intersect the structures 18 and 20. For a backprojection path 8 having N pixels this may be expressed as follows:

$$S_n = (P \times C_n) / \sum_{n=1}^{N} C_n \quad (2)$$

where: P=the signal sample value; and
C<sub>n</sub>=signal value of the composite image at the nth pixel along the backprojection path.

The numerator in equation (2) weights each pixel using the corresponding signal value in the composite image and the denominator normalizes the value so that all backprojected signal samples reflect the projection sums for the image frame and are not multiplied by the sum of the composite image.

A 3D embodiment of the invention is shown graphically in FIG. 4 for a single 3D projection view characterized by the view angles θ and φ. This projection is back projected along axis 16 and spread into a Radon plane 21 at a distance r along the back projection axis 16. Instead of a filtered back projection in which projection signal contour values are filtered and uniformly distributed into the successive Radon planes, along axis 16, the projection signal contour values are distributed in the Radon plane 21 using the information in the composite image. The composite image in FIG. 4 contains vessels 18 and 20. The weighted signal contour value is deposited at image location x, y, z in the Radon plane 21 based on the intensity at the corresponding location x, y, z in the composite image. This is a simple multiplication of the signal profile value by the corresponding composite image voxel value. This product is then normalized by dividing the product by the profile value from the corresponding image space profile formed from the composite image. The formula for the 3D reconstruction is $$I(x, y, z) = \sum (P(r, \theta, \phi) * C(x, y, z)_{(r,\theta,\phi)} / P_c(r, \theta, \phi)) \quad (3)$$

where the sum (Σ) is over all projections in the time frame and the x, y, z values in a particular Radon plane are calculated using the profile value P(r, θ, φ) at the appropriate r, θ, φ value for that plane. P<sub>c</sub>(r, θ, φ) is the corresponding profile value from the composite image and C(x, y, z)<sub>r, θ, φ</sub> is the composite image value at (r, θ, φ)

Another discovery of the present invention is that the highly constrained backprojection method is particularly useful in combination with the McKinnon and Bates method. The McKinnon and Bates method calls for the subtraction of the static tissue signals from the acquired projection views. This results in a set of sparse projection data from which a composite image may be reconstructed that contains a priori information limited to the structures of interest.

Another aspect of the present invention is the reconstruction of magnetic resonance image frames acquired during a cardiac gated scan with a 3D hybrid projection reconstruction pulse sequence. Projection views are acquired to sample k-space with radial trajectories in a 2D slice and phase encoding is employed to acquire multiple slices along an axial direction. A composite image is reconstructed for each of the multiple slice locations and these composite images are employed during the backprojection reconstruction of the 2D slices in each image frame.

BRIEF DESCRIPTION OF THE DRAWINGS

FIG. 12 is a flow chart of the steps for producing a composite image according to an embodiment of the present invention.

DETAILED DESCRIPTION OF THE PREFERRED EMBODIMENT

Figure 1:
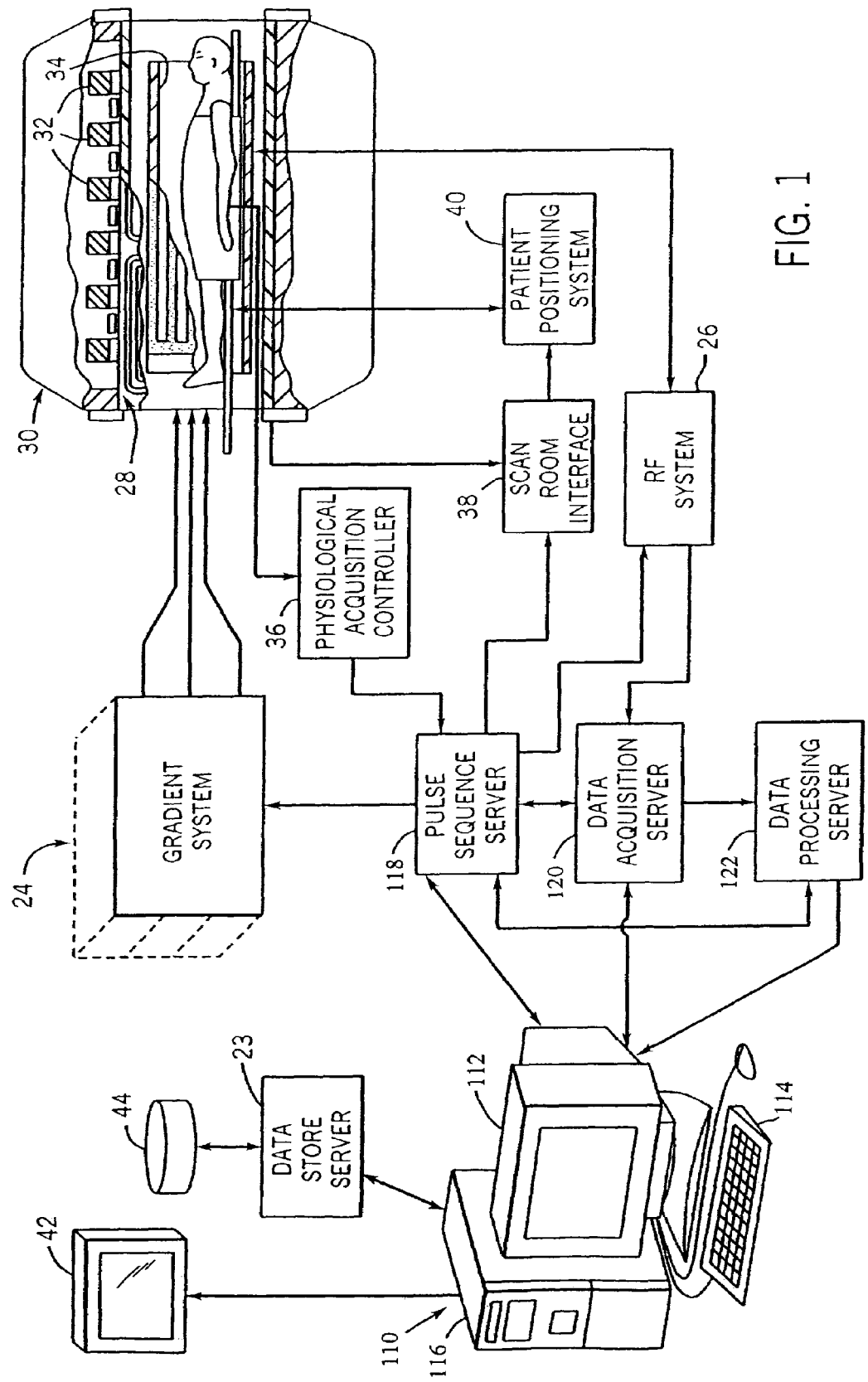
FIG. 1 is a block diagram of an MRI system which employs the present invention.
Figure 2:
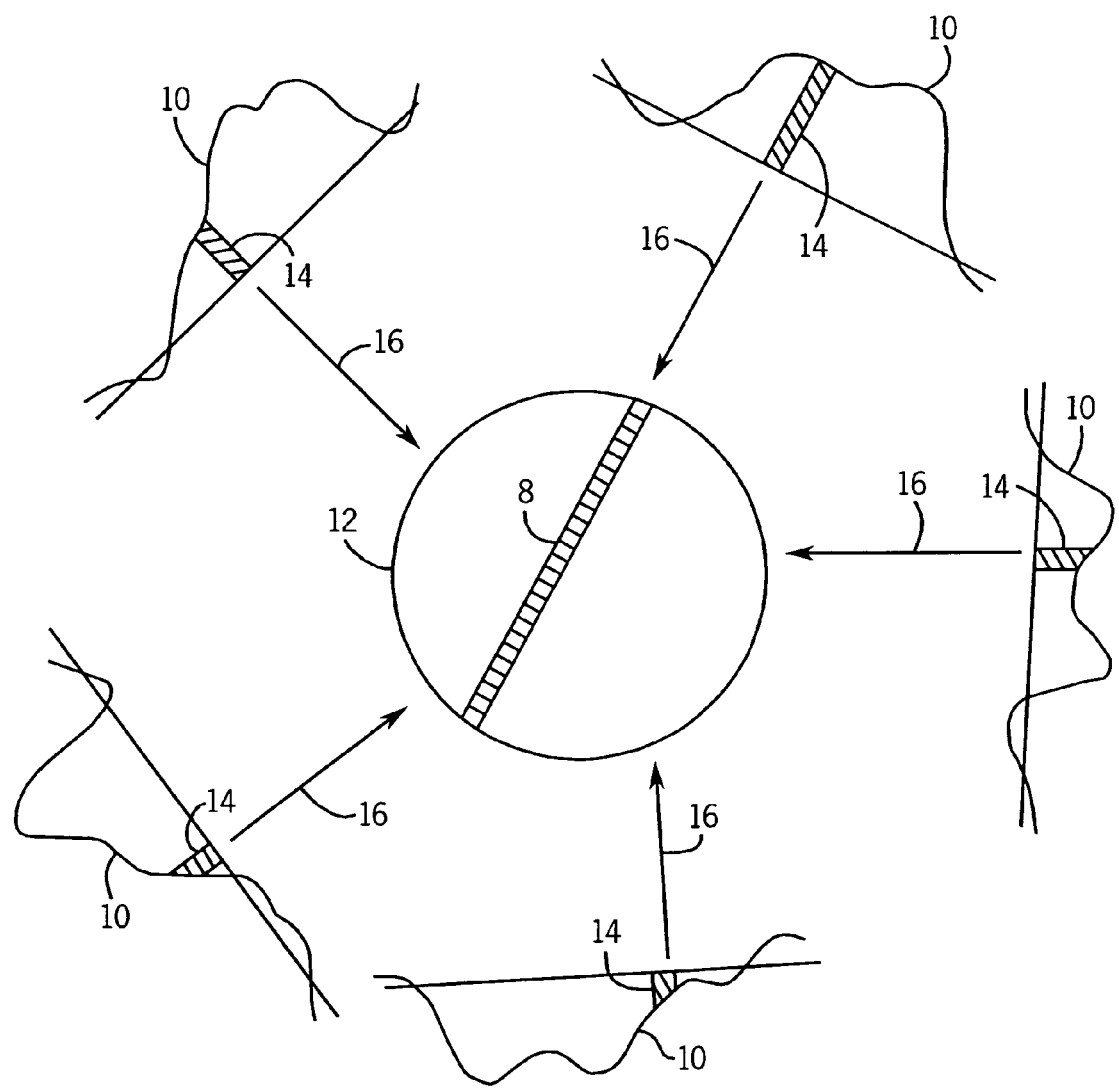
FIG. 2 is a pictorial representation of a conventional backprojection reconstruction method.

Referring particularly to FIG. 1, a preferred embodiment of the invention is employed in an MRI system. The MRI system includes a workstation 110 having a display 112 and a keyboard 114. The workstation 110 includes a processor 116 which is a commercially available programmable machine running a commercially available operating system. The workstation 110 provides the operator interface which enables scan prescriptions to be entered into the MRI system.

The workstation 110 is coupled to four servers: a pulse sequence server 118; a data acquisition server 120; a data processing server 122, and a data store server 23. In the preferred embodiment the data store server 23 is performed by the workstation processor 116 and associated disc drive interface circuitry. The remaining three servers 118,120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The workstation 10 and each processor for the servers 118, 120 and 122 are connected to a serial communications network. This serial network conveys data that is downloaded to the servers 118, 120 and 122 from the workstation 110 and it conveys tag data that is communicated between the servers and between the workstation and the servers. In addition, a high speed data link is provided between the data processing server 122 and the workstation 10 in order to convey image data to the data store server 23.

The pulse sequence server 118 functions in response to program elements downloaded from the workstation 110 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 118. The RF system 26 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels which may be connected to a corresponding plurality of local coils or to a corresponding plurality of coil elements in a coil array. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2-Q^2},$$

and the phase of the received NMR signal may also be determined:

$$\phi=\tan^{-1}Q/I.$$

The pulse sequence server 118 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs which receive these objects and converts them to objects that are employed by the run-time programs.

The digitized NMR signal samples produced by the RF system 26 are received by the data acquisition server 120. The data acquisition server 120 operates in response to description components downloaded from the workstation 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the workstation 110. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 42 which is located near the magnet assembly 30 for use by attending physicians. Batch mode images or selected real time images are stored in a host database on disc storage 44. When such images have been reconstructed and transferred to storage, the data processing server 122 notifies the data store server 23 on the workstation 110. The workstation 110 may be used by an operator to archive the images, produce films, or send the images via a network to other facilities.

Figure 5:
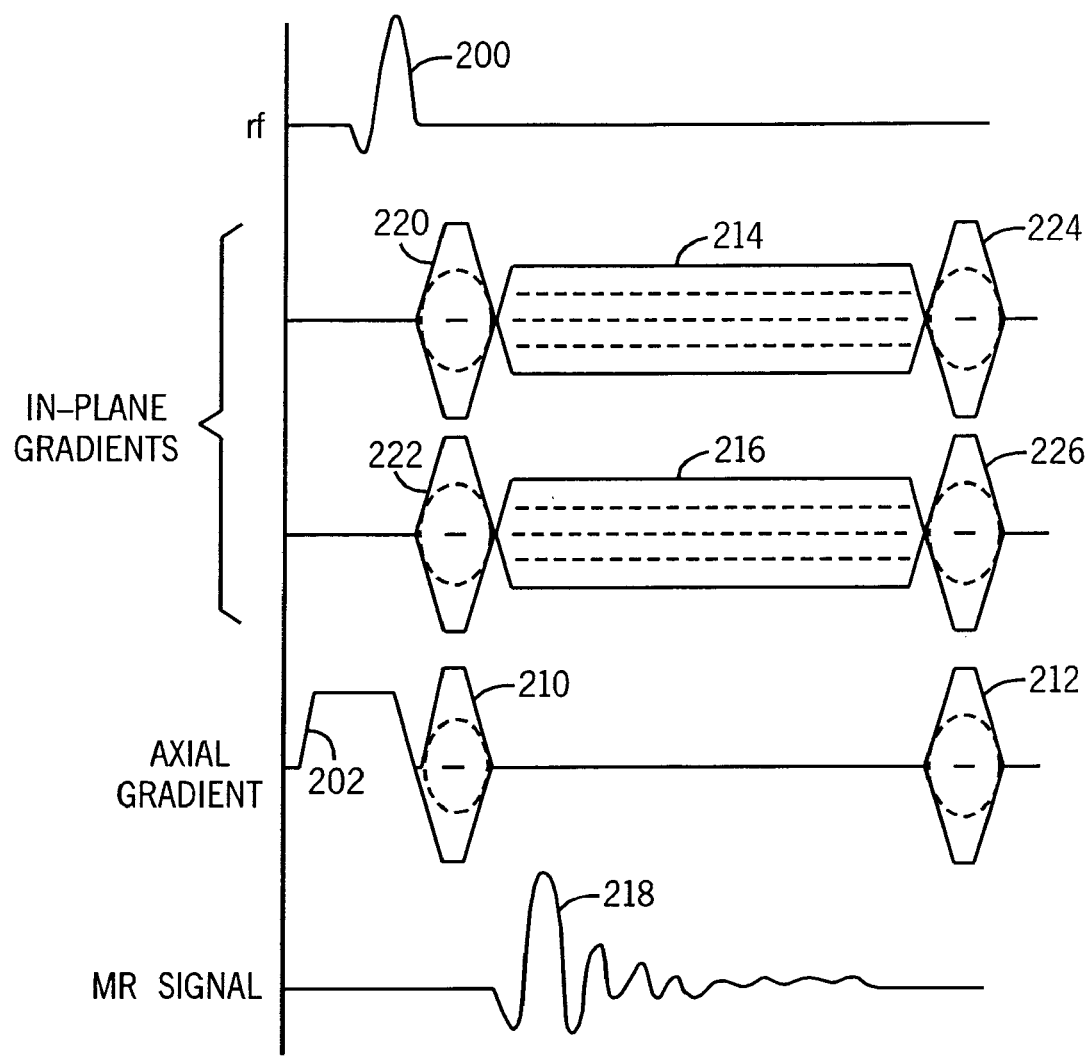
FIG. 5 is a graphic illustration of a hybrid PR pulse sequence performed by the MRI system of FIG. 1 when practicing the preferred embodiment of the present invention.

To practice the preferred embodiment of the invention NMR data is acquired using a projection reconstruction, or radial, pulse sequence shown in FIG. 5. This is a fast gradient-recalled echo pulse sequence in which a selective, asymmetrically truncated sinc rf excitation pulse 200 is produced in the presence of a slice-select gradient 202. The flip angle of the rf pulse 200 is set near the Ernst angle for $T_1$ shortened blood which is typically 30° to 40°.

Figure 6:
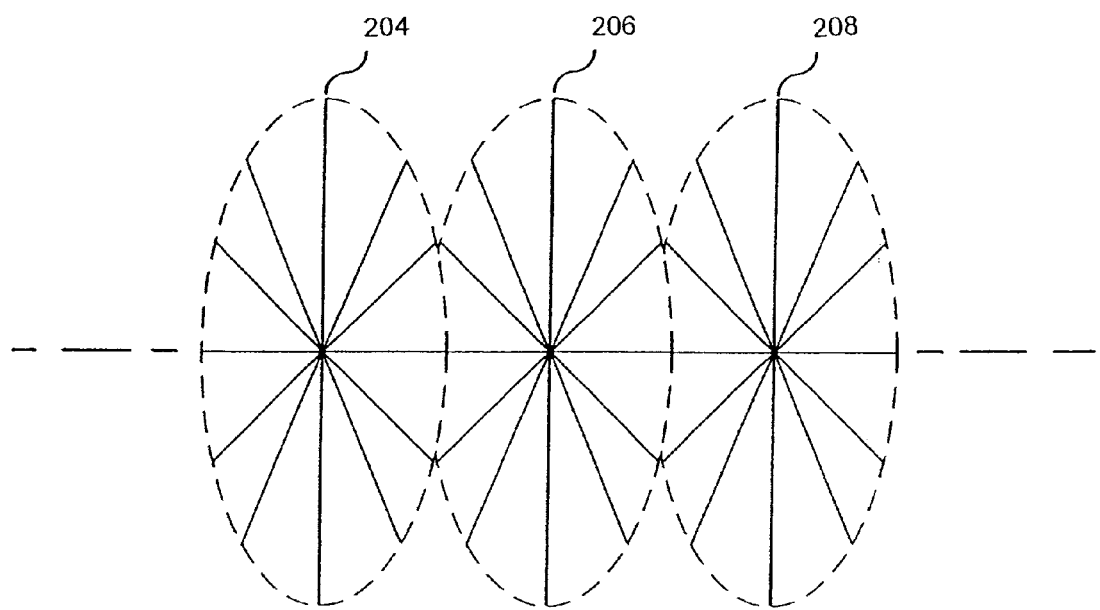
FIG. 6 is a pictorial representation of k-space sampling using the hybrid pulse sequence of FIG. 3.

This pulse sequence may be used to acquire a single 2D slice by sampling in a single k-space circular plane, but in the preferred embodiment a plurality of circular k-space planes are sampled as shown at 204, 206 and 208 in FIG. 6. When multiple 2D slices are acquired the axial gradient 202 is a slab select gradient followed by a phase encoding gradient lobe 210 and a rewinder gradient lobe 212 of opposite polarity. This axial phase encoding gradient 210 is stepped through values during the scan to sample from each of the 2D k-space planes 204, 206 and 208.

Two in-plane readout gradients 214 and 216 are played out during the acquisition of an NMR echo signal 218 to sample k-space in a 2D plane 204, 206 or 208 along a radial trajectory. These in-plane gradients 214 and 216 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 220 and 222 and followed by a rewinder gradient lobe 224 and 226.

It should be apparent to those skilled in the art that sampling trajectories other than the preferred straight line trajectory extending from one point on the k-space peripheral boundary, through the center of k-space to an opposite point on the k-space peripheral boundary may be used. One variation is to acquire a partial NMR echo signal 218 which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715,1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should also be apparent that the present invention may be employed with 3D as well as 2D versions of these sampling methods and references to the term "pixel" as used hereinafter is intended to refer to a location in either a 2D or a 3D image.

Figure 7:
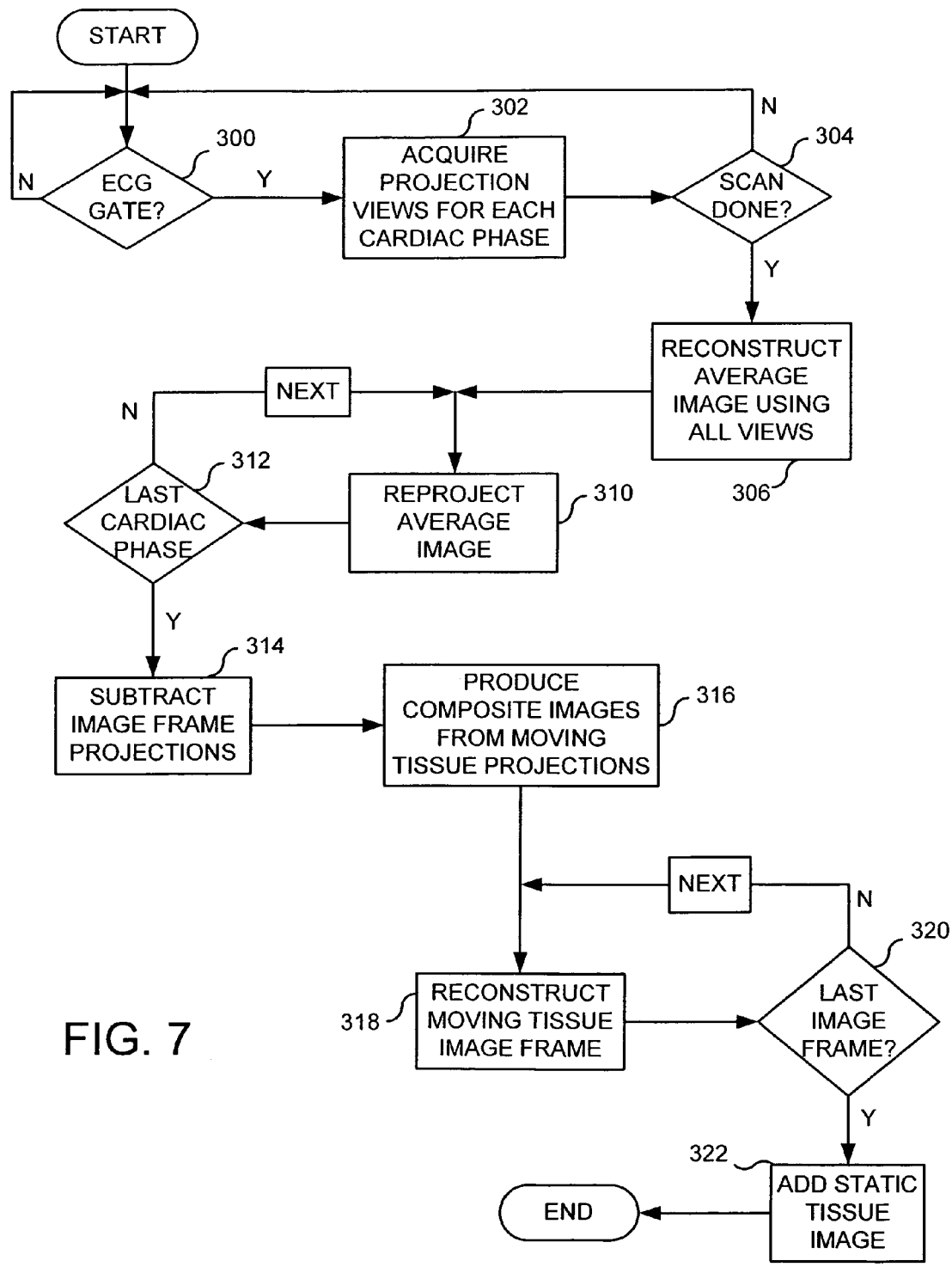
FIG. 7 is a flow chart of the steps in a preferred embodiment of the present invention.
Figure 8:
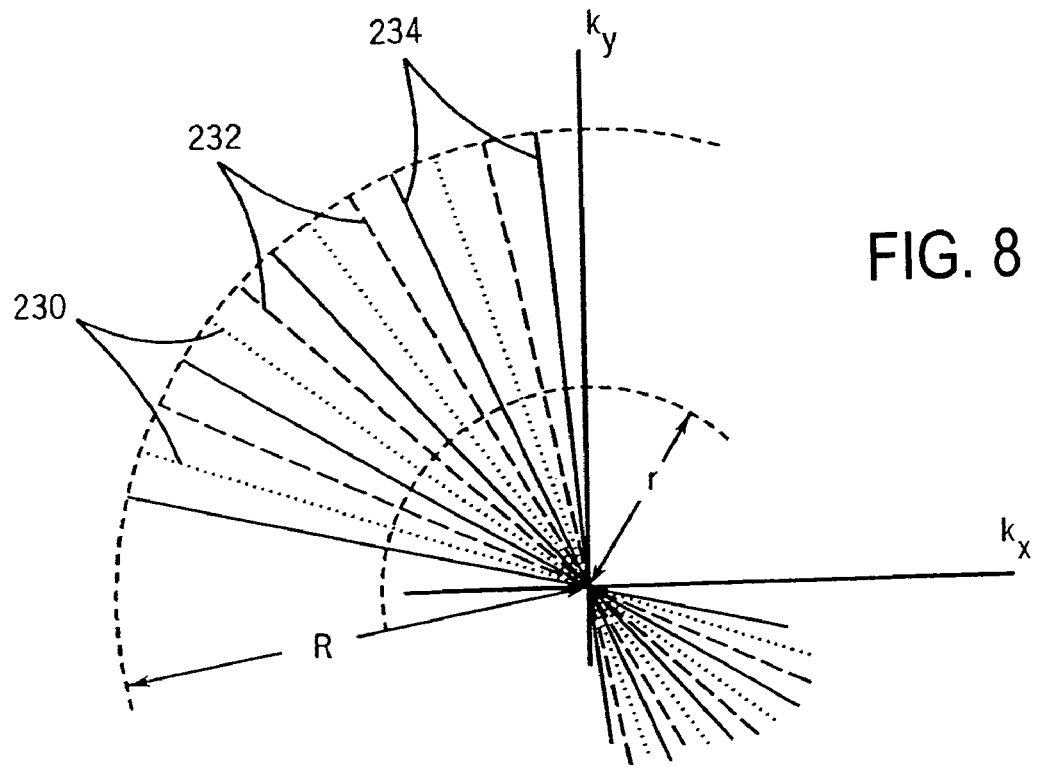
FIG. 8 is a pictorial representation of interleaved sampling of k-space with radial sampling trajectories.

Referring particularly to FIG. 7, a series of cardiac gated image frames are acquired that depict the heart at a corresponding number of different cardiac phases. As indicated at decision block 300, the system waits for an ECG gating signal and when the signal is received the pulse sequence of FIG. 5 is performed to acquire projection views of the moving heart and surrounding stationary tissues from each of a plurality (e.g., N=20) cardiac phases as indicated at process block 302. Three 2D slices are effectively acquired at each cardiac phase using this particular pulse sequence, and the projection views are interleaved and equally spaced as shown in FIG. 8, where the dotted lines 230 indicate the k-space sampling trajectories acquired for one slice, dashed lines 232 indicate the k-space sampling trajectories acquired for a second slice and solid lines 234 indicate the k-space sampling pattern for the third slice. The acquisition continues until the prescribed number of projection views (e.g., n=30) are acquired for each of the three 2D slices at each cardiac phase as detected at decision block 304. As shown at block 305 in FIG. 9, N=20 image frames are thus acquired with n=30 interleaved projection views in each 2D slice image frame. Not only are the projection views acquired at each cardiac phase interleaved as described above, but they are also interleaved with the projection views acquired at the other cardiac phases.

There are many different ways to produce a list of projection view angles φ during the scan that will interleave all the acquired views. The view angles φ will depend on such factors as the number of cardiac phases (N) to be acquired during each heartbeat, the number of projection views to be acquired for each cardiac phase during one heart beat ($n_{pr}$), and the number of heart beats (H) during the scan. The formula used in the preferred embodiment to calculate the view angle for the $n^{th}$ cardiac phase in the $k^{th}$ heartbeat is:

$$\phi = \Delta_1 \times K + \Delta_2 \times B(n) + [0:180/n_{pr}:180]$$

where $$\Delta_1 = 180/(H \times n_{pr})$$

$$\Delta_2 = 180/(H \times N \times n_{pr})$$

B(n)=bitreversal algorithm for generating pseudo random permutation of a sequence of integers. The view angles φ for each of the slices are also interleaved, and this is achieved by incrementing the starting angle in each slice by 180°/number of slices.

Figure 9:
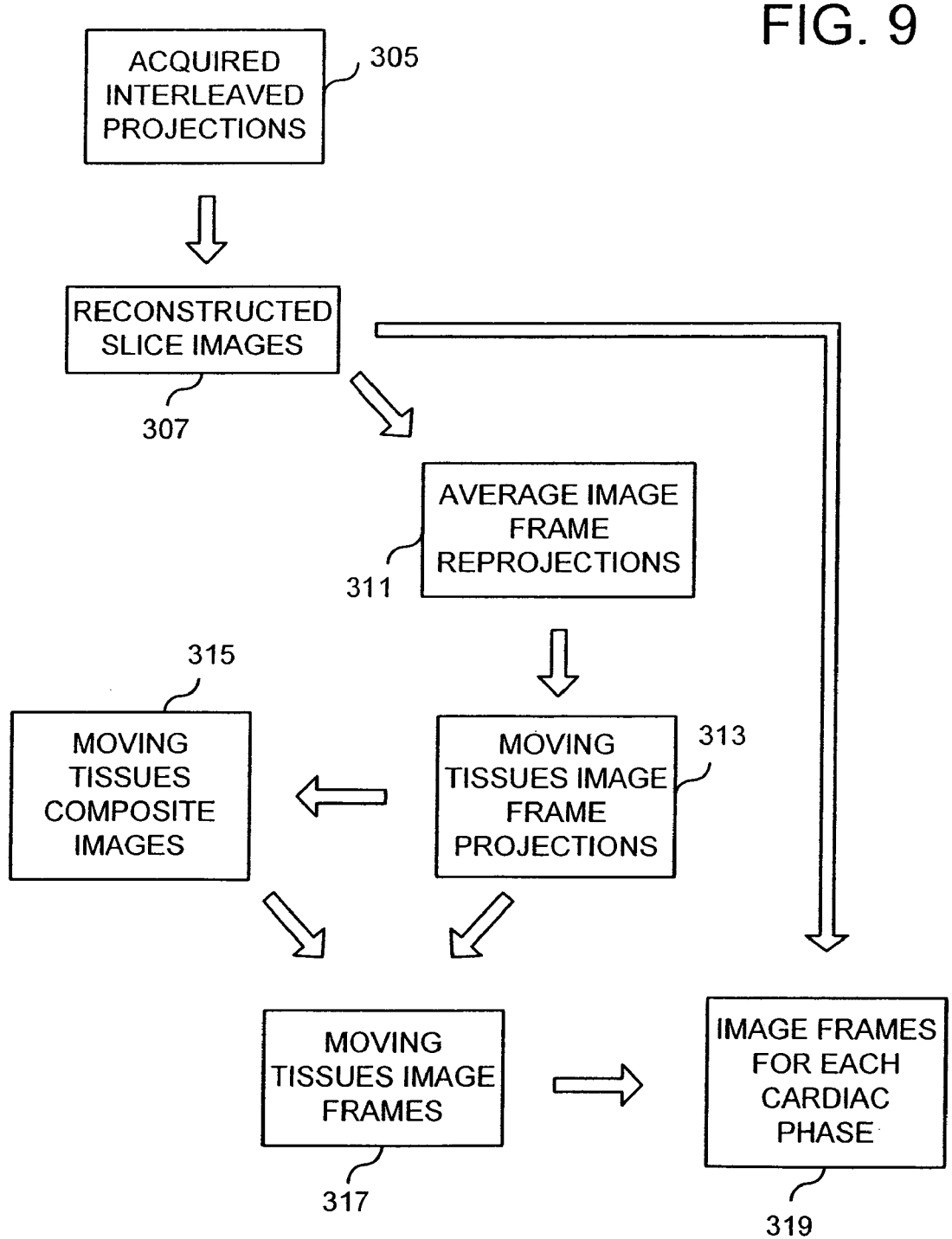
FIG. 9 is a chart showing the data structures that are produced by the method of FIG. 7.

Referring still to FIGS. 7 and 9, an image 307 is reconstructed using all the acquired projection views (n×N) for each slice location as indicated at process block 306. This is a conventional reconstruction process in which the acquired NMR signals are first Fourier transformed along the axial gradient direction to produce projections at the three slice locations along that axis. The radial k-space sample points for each 2D slice are then regridded to a Cartesian grid and then a two-dimensional Fourier transformation is performed. The resulting average image will depict the heart as a blur due to its motion, but because all of the acquired, interleaved projection views at each slice in each cardiac phase are used in the reconstruction, the static structures will be depicted accurately and with few artifacts.

Figure 10:
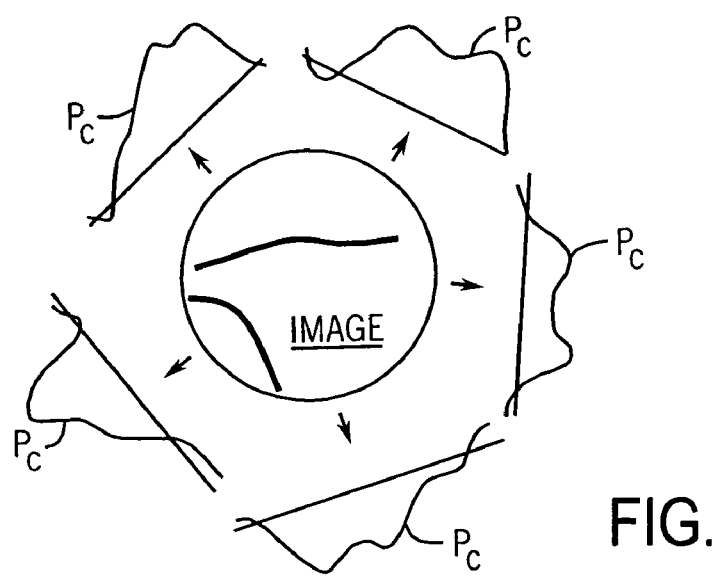
FIG. 10 is a pictorial representation of a reprojection step in the method of FIG. 7.

As indicated at process block 310, the average image 307 is reprojected at all the projection view angles for one of the N cardiac phases. This is illustrated in FIG. 10 and is accomplished with a conventional Radon transformation as described, for example, in "Computed Tomography Principles, Design, Artifacts and Recent Advances", Jiang Hsieh, SPIE Press 2003, Chapter 3. A projection contour is thus produced at each view angle acquired for each slice at this cardiac phase. The reprojection step 310 is repeated for each cardiac phase, and when the last cardiac phase projection has been reprojected as detected at decision block 312, average image frame reprojections have been produced as indicated in FIG. 9 at block 311.

As indicted at process block 314, the next step is to subtract each of the average image reprojections from the corresponding acquired projections 305. This results in a set of n=30 projection views for each 2D slice in each of the acquired N=20 cardiac phases which depict only the moving tissues as indicated at block 313. The signals from the static tissues are subtracted out and the remaining signals are essentially high pass filtered moving tissue signals. This is a "sparse" data set in that only the moving structures in the FOV are embodied in these projection views for each 2D slice image frame.

Composite images are reconstructed next as indicated at process block 316 by performing a conventional image reconstruction using moving tissue projection views 313. A composite image is reconstructed for each 2D slice image frame at each cardiac phase as will be described in more detail below. Because the composite images 315 are reconstructed from a large number of different projection views, they have a much higher SNR than an image reconstructed in a conventional manner from n=30 projections in a single 2D slice image frame.

As indicated at process block 318, the next step is to reconstruct each moving tissue 2D slice image frame by performing a highly constrained backprojection of each of the n=30 moving tissue projections. This step is described in more detail below and the result is a good image of the moving structures in the FOV as indicated by block 317. Each moving tissue 2D slice image frame at each cardiac phase is reconstructed in this manner until the last image frame is reconstructed as detected at decision block 320. As indicated at process block 322, the final step is to combine each moving tissue image frame 317 with the average image 307 to form the final image frames 319 for each cardiac phase. This is accomplished by adding the values at corresponding pixels in the images. This adds the good static tissue signals and it adds back the low frequency moving tissue signals previously subtracted out in process block 314.

As discussed above, a composite image is produced for each of the moving tissue 2D slice image frames to provide a priori information regarding the subject in the FOV. The trick is to select moving tissue projection views that have been acquired and that accurately depict the subject at the 2 D slice location. The projection views for the current 2D slice image frame are included, but because the subject is moving, care must be taken in selecting additional projection views to be included in the composite image.

Referring particularly to FIG. 12, projection views from the same slice location acquired in adjacent cardiac phases are selected to be included in a composite image based on the amount of subject motion that has occurred. As indicated at process block 400, the center of mass ("COM") of each moving tissue projection view is calculated to roughly locate the position of the moving tissues. This calculation is done by utilizing the fact that the projection of the COM of an object onto a Radon line can be obtained from the averaged first moment of the corresponding sinogram:

$$COM_x{}^* \cos\theta + COM_y{}^* \sin\theta = \int rR(r,\theta)\,dr / \int R(r,\theta)\,dr$$

where: $COM_x$ $COM_y$ =coordinates of the COM $R(r,\theta)$ =Radon projection (sinogram).

A loop is then entered in which the difference between the COM of projection views in the current 2D slice image frame and the COM of projection views in an adjacent cardiac phase is calculated as indicated at process block 402. If this difference is below a preset magnitude as determined at decision block 414, the moving tissue projection views for that adjacent cardiac phase are added to the composite image as indicated at process block 406. This evaluation is repeated for other adjacent cardiac phases as indicated at process block 408 until the preset motion value is exceeded as determined at decision block 404.

The number of moving tissue projection views included in the composite image for a particular moving tissue 2d image frame will depend on the amount of subject motion that is occurring. During diastole there is little subject motion and the projection views from as many as six cardiac phases may be included and a very high SNR composite image will result. On the other hand, during rapid heart motion, projection views from as few as one or two cardiac phases may be successfully combined. Regardless of the number of interleaved projection views included, the composite image for the current 2D slice image frame is reconstructed as indicated at process block 410. This is a conventional image reconstruction, which in the preferred embodiment is a regridding followed by a two-dimensional Fourier transformation as described above.

The system loops back to reconstruct composite images for each acquired 2D slice image frame as indicated at process block 412. When all the compositeimages are reconstructed, as indicated at decision block 414, the process iscomplete.

Figure 3:
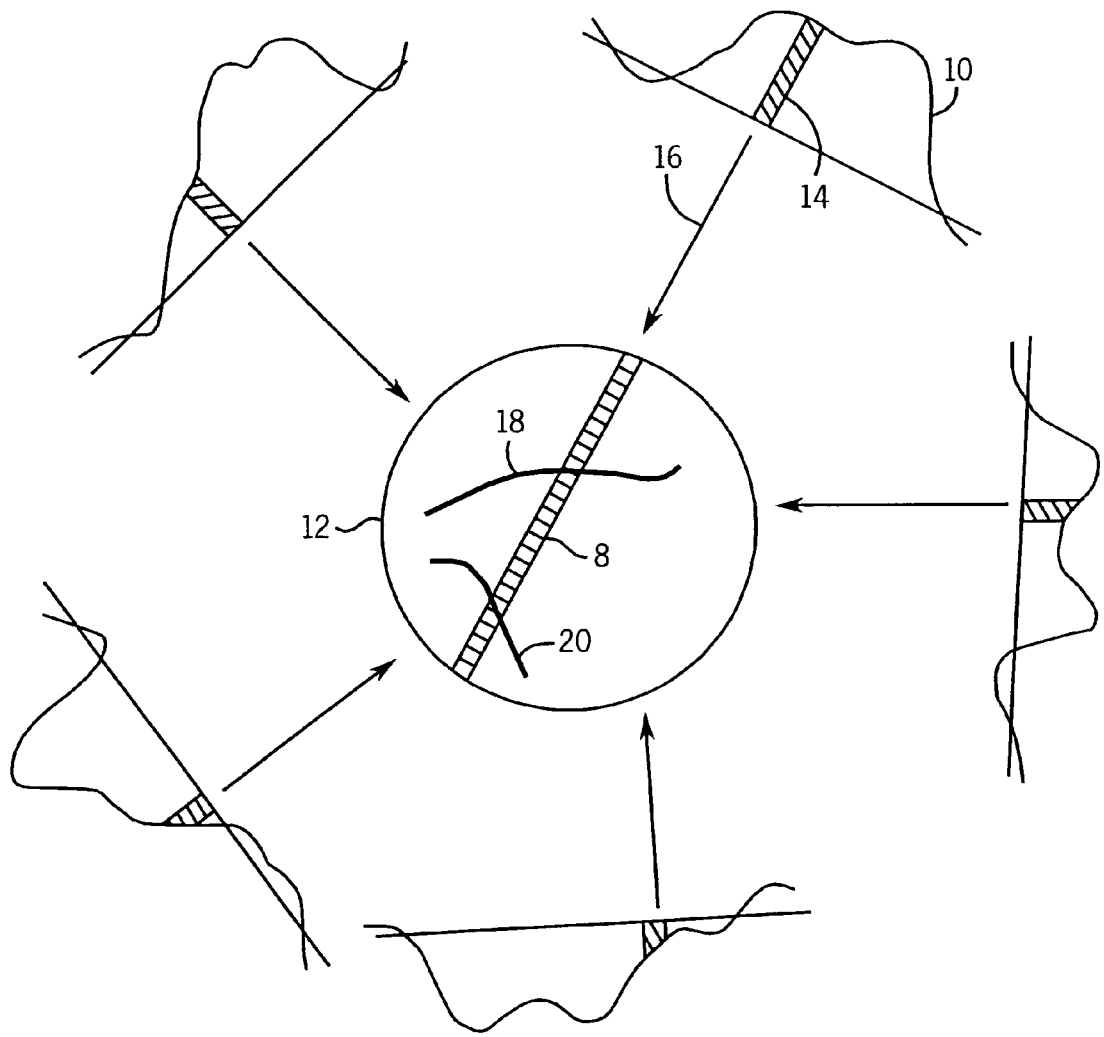
FIG. 3 is a pictorial representation of the backprojection method according to the present invention for a 2D PR image reconstruction.
Figure 4:
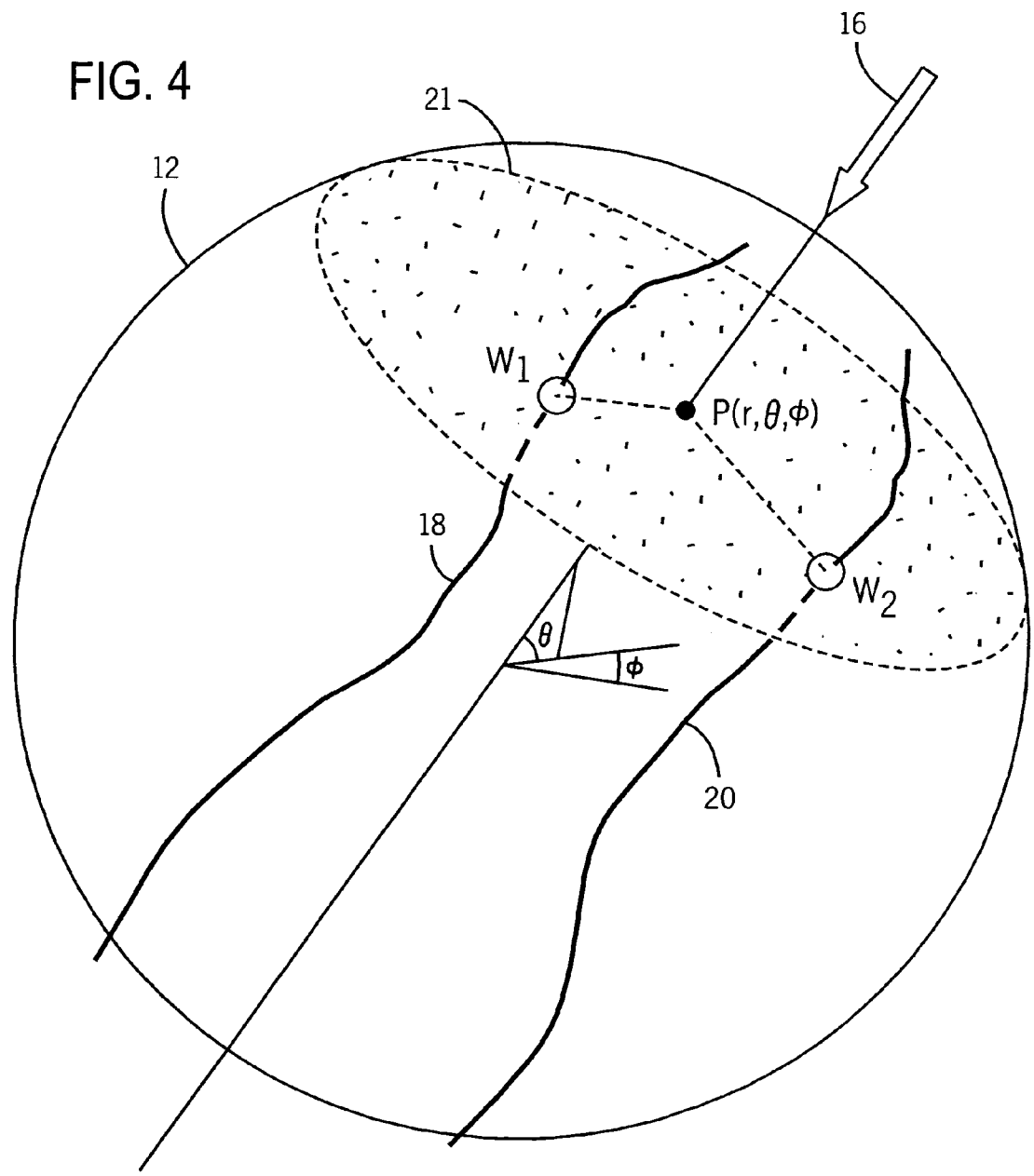
FIG. 4 is a pictorial representation of the backprojection method for a 3DPR image reconstruction.
Figure 11:
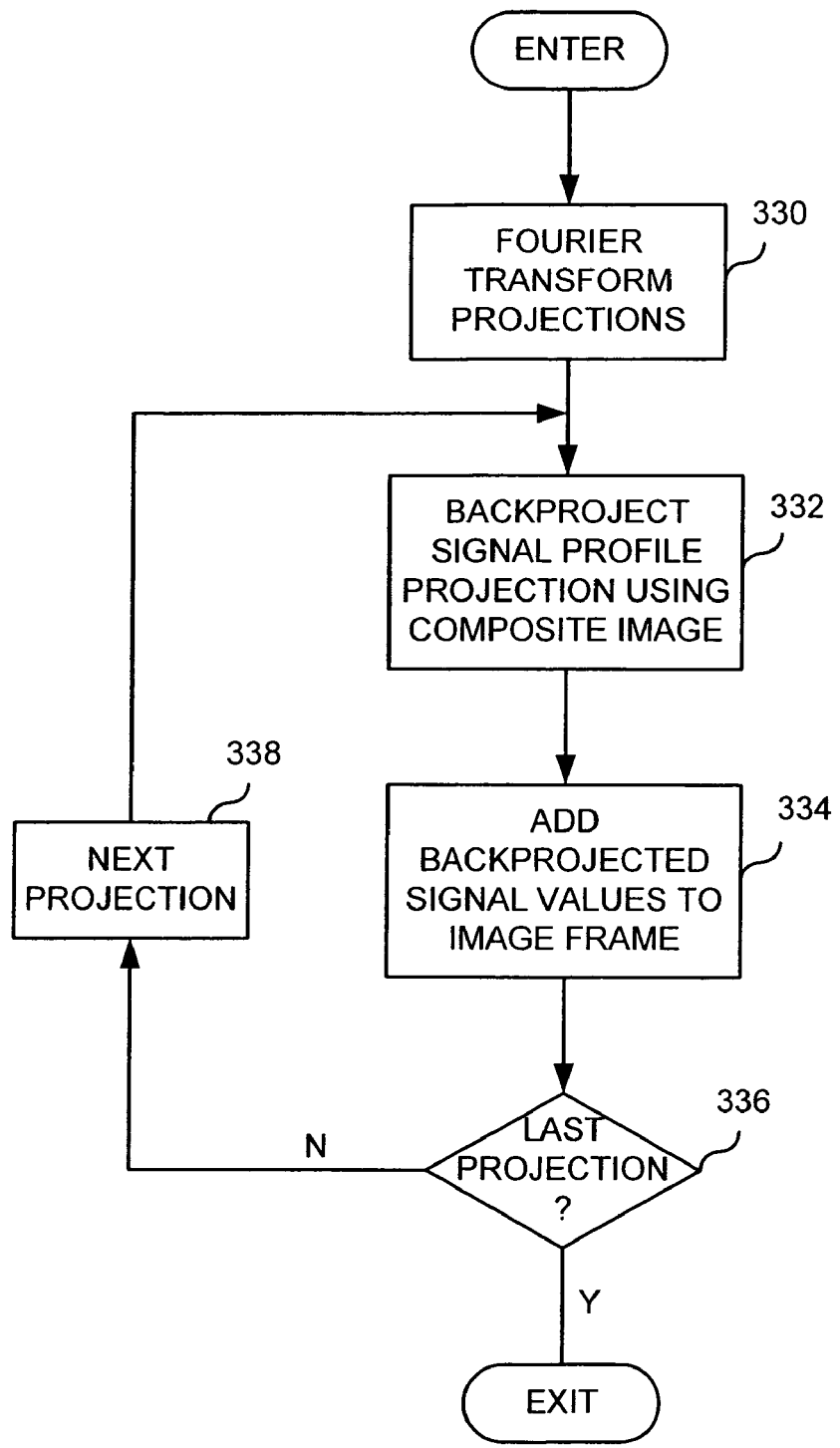
FIG. 11 is a flow chart of the steps for reconstructing a 2D image frame according to the present invention.

The highly constrained backprojection reconstruction method discussed above uses the corresponding composite image to constrain the backprojection of each moving tissue projection view 313. Referring particularly to FIG. 11, the first step is to transform the moving tissue image frame k-space projections to Radon space by Fourier transforming them as indicated at process block 330. The result is a set of signal profiles 10 as depicted in FIG. 3. As indicated at process block 332, each of these signal profiles is then backprojected into the FOV as depicted by path 8 in FIG. 3. This backprojection is weighted by the composite image as described above with reference to equation (2). That is, the backprojection value (P) at any pixel (n) is weighted by the normalized magnitude ($C_n$) of the same pixel in the composite image.

As indicated at process block 334, the backprojected signal values ($S_n$) are then added to a 2D slice image frame that is being reconstructed. The system loops back at decision block 336 to backproject the next signal profile 10 as indicated at process blocks 338 and 332. The signal values ($S_n$) of all the backprojected signal profiles 10 are, therefore, added to the image frame with a weighting determined by corresponding pixel values in the higher quality composite image 315. The composite image 315 is higher in quality because it is reconstructed from far more projection views and this results in fewer artifacts. The composite image 315 is also higher quality because the projection views used to reconstruct it are acquired over a much longer time span. Generally, the SNR of an image frame is proportional to the square root of its acquisition duration, and the higher SNR of the composite image 315 is conveyed to the image frame through this unique reconstruction process.

While the preferred embodiment of the invention is employed in an MRI system, it should be apparent that the invention may also be embodied in a CT system. As with the MRI system described above, interleaved cardiac gated projection views are acquired with the CT system at one or more cardiac phases and at one or more axial slice locations. These are used to reconstruct one or more frame images using nearly the same steps described above and shown in FIG. 7. Instead of the regridding and Fourier transformation of the acquired k-space projection views described above, the Radon space projection views acquired with a CT scanner are reconstructed into an image using a conventional filtered backprojection method.

It should also be apparent that the present invention may be used to reconstruct either 2D slice images from acquired projection data or 3D images. In the latter case the highly constrained backprojection step will employ the 3D method of equation (3) rather than the 2D method of equation (2) described above.

The invention claimed is:

1. A method for producing an image of a moving subject positioned in a field of view (FOV) of a medical imaging system, the steps comprising:
   a) acquiring with the medical imaging system a set of projection views of the subject for each of a series of image frames;
   b) producing from the projection views acquired in step a) corresponding moving tissue projection views in which substantially only moving tissues are depicted;
   c) producing from more than one set of the projection views acquired in step a) an average image;
   d) reconstructing a composite image for one of said image frames using moving tissue projection views corresponding to the projection views acquired for said image frame plus other selected moving tissue projection views;
   e) reconstructing a moving tissue image for said image frame by:
      e)i) back projecting the moving tissue projection views corresponding to the projection views acquired for said image frame and weighting the value backprojected into each image pixel by the value of the corresponding pixel in the composite image; and
      e)ii) summing the backprojected values for each image pixel; and
   f) combining the moving tissue image and the average image.

2. The method as recited in claim 1 in which step c) includes reconstructing the average image from a sufficient number of projection views acquired in step a) that static tissues in the FOV are depicted with few artifacts.

3. The method as recited in claim 1 in which step b) includes: b)i) reprojecting the average image to produce average image reprojections; and b)ii) subtracting average image reprojections from corresponding acquired projection views to produce corresponding moving tissue projection views.

4. The method as recited in claim 3 is which substantially all the projection views acquired in step a) are used to reconstruct the average image in step c).

5. The method as recited in claim 4 in which the moving tissue projection views are produced in step b) by reprojecting the average image at each of the view angles of the projection views acquired in step a).

6. The method as recited in claim 1 in which the acquisitions in step a) are cardiac gated and the series of image frames depict the moving subject at a succession of cardiac phases.

7. The method as recited in claim 6 in which the projection views acquired in step a) are acquired over a plurality of heartbeats.

8. The method as recited in claim 7 in which the medical imaging system is a magnetic resonance imaging system.

9. The method as recited in claim 1 in which said other moving tissue projection views are selected in step d) by:
   d)i) determining how much the subject has moved while acquiring each set of projection-views relative to the subject's position when the projection views for said image frame were acquired; and
   d)ii) selecting moving tissue projection views that were acquired when the subject was within a predetermined distance from said image frame position.

10. The method as recited in claim 1 in which steps d), e) and f) are repeated to produce additional images from the other sets of image frame projection views.

11. The method as recited in claim 1 in which each weighted image pixel backprojected value $S_n$ is calculated in step e) as $S_n = (P \times C_n)/\sum_{n=1}^{N} C_n$ where P=the projection view being backprojected; $C_n$=corresponding pixel value in the contour image; $S_n$=the value of the no pixel along the backprojecting path; and N=total number of pixels along the backprojection path.

12. The method as recited in claim 1 in which the projection views acquired in step a) are interleaved.

13. The method as recited in claim 1 in which the moving tissue projection views used in step d) are interleaved.

14. The method as recited in claim 1 in which sets of projection views acquired in step a) correspond to a slice location acquired at each of a plurality of cardiac phases.

15. The method as recited in claim 14 in which the projection views acquired for said slice location are interleaved.

16. The method as recited in claim 15 in which the composite image is formed using moving tissue projection views corresponding to interleaved projection views acquired for said slice.

17. The method as recited in claim 16 in which steps d), e) and f) are repeated to produce an image depicting the moving subject at each of the cardiac phases.

18. The method as recited in claim 16 in which sets of projection views acquired in step a) correspond to additional slice locations acquired at each of the plurality of cardiac phases and steps d), e) and f) are repeated to produce an image depicting the moving subject at each of the slice locations.

19. The method as recited in claim 18 in which steps d), e) and f) are repeated to produce an image depicting the moving subject at each slice location at each of the cardiac phases.

* * * * *

UNITED STATES PATENT AND TRADEMARK OFFICE
CERTIFICATE OF CORRECTION

PATENT NO. : 7,647,088 B2  Page 1 of 1
APPLICATION NO. : 11/516957
DATED : January 12, 2010
INVENTOR(S) : Mistretta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 375 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,647,088 B2
APPLICATION NO. : 11/516957
DATED : January 12, 2010
INVENTOR(S) : Charles A. Mistretta et al.

Page 1 of 1

It is certified that error appears in the above-identified patent and that said Letters Patent is hereby corrected as shown below:

In the Specification

Column 1, Lines 18-20:
Delete the phrase:
"This invention was made with government support under Grant No. NIH HL072260. The U.S. Government has certain rights in this invention."

And replace with:
--This invention was made with government support under HL072260 awarded by the National Institutes of Health. The government has certain rights in the invention.--.

Signed and Sealed this
Eighth Day of December, 2020

Andrei Iancu
*Director of the United States Patent and Trademark Office*